United States Patent
Chiao

(10) Patent No.: US 10,561,342 B2
(45) Date of Patent: Feb. 18, 2020

(54) SYSTEMS AND METHODS FOR DETECTING TREMORS

(71) Applicant: Jung-Chih Chiao, Austin, TX (US)

(72) Inventor: Jung-Chih Chiao, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 405 days.

(21) Appl. No.: 15/269,353

(22) Filed: Sep. 19, 2016

(65) Prior Publication Data

US 2017/0079561 A1    Mar. 23, 2017

Related U.S. Application Data

(60) Provisional application No. 62/221,395, filed on Sep. 21, 2015.

(51) Int. Cl.
*A61B 5/00* (2006.01)
*A61B 5/11* (2006.01)

(52) U.S. Cl.
CPC .......... *A61B 5/1101* (2013.01); *A61B 5/4082* (2013.01); *A61B 5/7246* (2013.01); *A61B 5/7257* (2013.01); *A61B 2560/0223* (2013.01)

(58) Field of Classification Search
CPC ....... A61B 5/1101; A61B 5/05; A61B 5/4082; A61B 2560/0223; A61B 5/7257; A61B 5/7246

See application file for complete search history.

(56) References Cited

U.S. PATENT DOCUMENTS

| | | | | |
|---|---|---|---|---|
| 2002/0115944 A1* | 8/2002 | Mendes | ............... | A61B 5/06 600/594 |
| 2007/0236213 A1* | 10/2007 | Paden | ............... | A61B 3/16 324/228 |
| 2013/0338539 A1* | 12/2013 | Bailey | ............... | A61B 5/1101 600/595 |
| 2015/0065841 A1* | 3/2015 | Lee | ............... | A61B 5/053 600/388 |

OTHER PUBLICATIONS

Shi, et al., "A contactless detector for tremors", 2015 IEEE MTT-S International Microwave Workshop Series on RF and Wireless Technologies for Biomedical and Healthcare Applications, Taipei. Sep. 21-23, 2015.

(Continued)

*Primary Examiner* — Charles A Marmor, II
*Assistant Examiner* — David Joseph Fernandez-Fidalgo
(74) *Attorney, Agent, or Firm* — Thomas | Horstemeyer, LLP

(57) ABSTRACT

In one embodiment, a system for detecting tremors includes a contactless tremor detector, the detector including an oscillator circuit having a sensing coil, an oscillator configured to generate alternating electromagnetic fields, and a frequency counter configured to sense the resonant frequency of the oscillator circuit as the resonant frequency changes in response to movement of a body part of an individual adjacent to the sensing coil, wherein the system is configured to determine a frequency of movement of the body part from the sensed resonant frequency for the purpose of determining if the individual is experiencing tremors.

10 Claims, 7 Drawing Sheets

(56) References Cited

OTHER PUBLICATIONS

Pierleoni, et al., "A real-time system to aid clinical classification and quantification of tremor in Parkinson's disease", IEEE 2014.
Sample, et al., "Analysis, Experimental Results, and Range Adaptation of Magnetically Coupled Resonators for Wireless Power Transfer", IEEE Transactions on Industrial Electronics, vol. 58, No. 2, Feb. 2011.
Deuschl, et al., "Consensus statement of the movement disorder society on tremor", Movement Disorders, vol. 13, Suppl 3, 1998.
Jeon, et al., "Distance estimation from acceleration for quantitative evaluation of Parkinson tremor", 33rd Annual International conference of the IEEE EMBS, 2011.
Schauber, et al., "Measurement of mutual inductance from the frequency dependence of impedance of AC couple circuits using a digital dual-phase lock-in amplifier", American Journal of Physics, 2008.
Patel, et al., "Monitoring Motor fluctuations in patients with Parkinson's Disease using wearable sensors", IEEE transactions on information technology in Biomedicine, vol. 13, No. 6, 2009.
Ding, et al. "Realization of numeral eddy current sensor modeling", 2012 5th International symposium on comutational intelligence and design, 2012.
IEEE Guide for Safety in AC substation grounding, IEEE Std 80-2000. IEEE power of engineering society, Jan. 30, 2000.

\* cited by examiner

SYSTEMS AND METHODS FOR DETECTING TREMORS

CROSS-REFERENCE TO RELATED APPLICATION

This application claims priority to co-pending U.S. Provisional Application Ser. No. 62/221,395, filed Sep. 21, 2015, which is hereby incorporated by reference herein in its entirety.

BACKGROUND

There are currently no standard diagnostic tools in clinical practice that can be used to quantitatively assess tremors, such as those caused by Parkinson's disease or fatigue. In current practice, symptoms are observed and evaluated with clinical protocols, but the results are subjective and can differ from person to person.

The frequency distribution of tremor syndromes has been investigated based on etiology. Voluntary hand movements range between 0 and 2 Hz while pathological tremors range between 3 and 12 Hz. Although detecting pathological tremors may help early diagnosis of diseases, such as Parkinson's disease, the frequency range of such tremors makes it difficult to observe tremors with the eyes.

Recently, research has been conducted using accelerometers with the goal of detecting the frequencies of tremors. For example, handheld devices having embedded accelerometers, such as smart phones, have been proposed to monitor hand tremors.

These devices, however, present an additional load, physically or subconsciously, to the patients who may not completely relax their muscles. This makes it more difficult to detect the tremors. Aside from that, the amplitude of the hand tremor cannot be accurately detected using an accelerometer, which detects the acceleration of an object instead of its motion.

From the above discussion, it can be appreciated that it would be desirable to have a system and method for accurately detecting tremors.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have a system and method for accurately detecting tremors. Disclosed herein are examples of such systems and methods. In some embodiments, a tremor detection system comprises a contactless tremor detector that includes an oscillator circuit. The oscillator circuit includes a sensing coil next to which a patient can place his or her hand (or other body part). The oscillator circuit generates alternating electromagnetic fields that generate an eddy current density on the surface of the user's hand. The magnetic fields generated by the eddy current couple back to the sensing coil and change the resonant frequency of the circuit. The changing resonant frequency can then be used to determine the distance of the hand from the coil as a function of time, which can then be converted into a frequency that can provide an indication of the presence of tremor.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
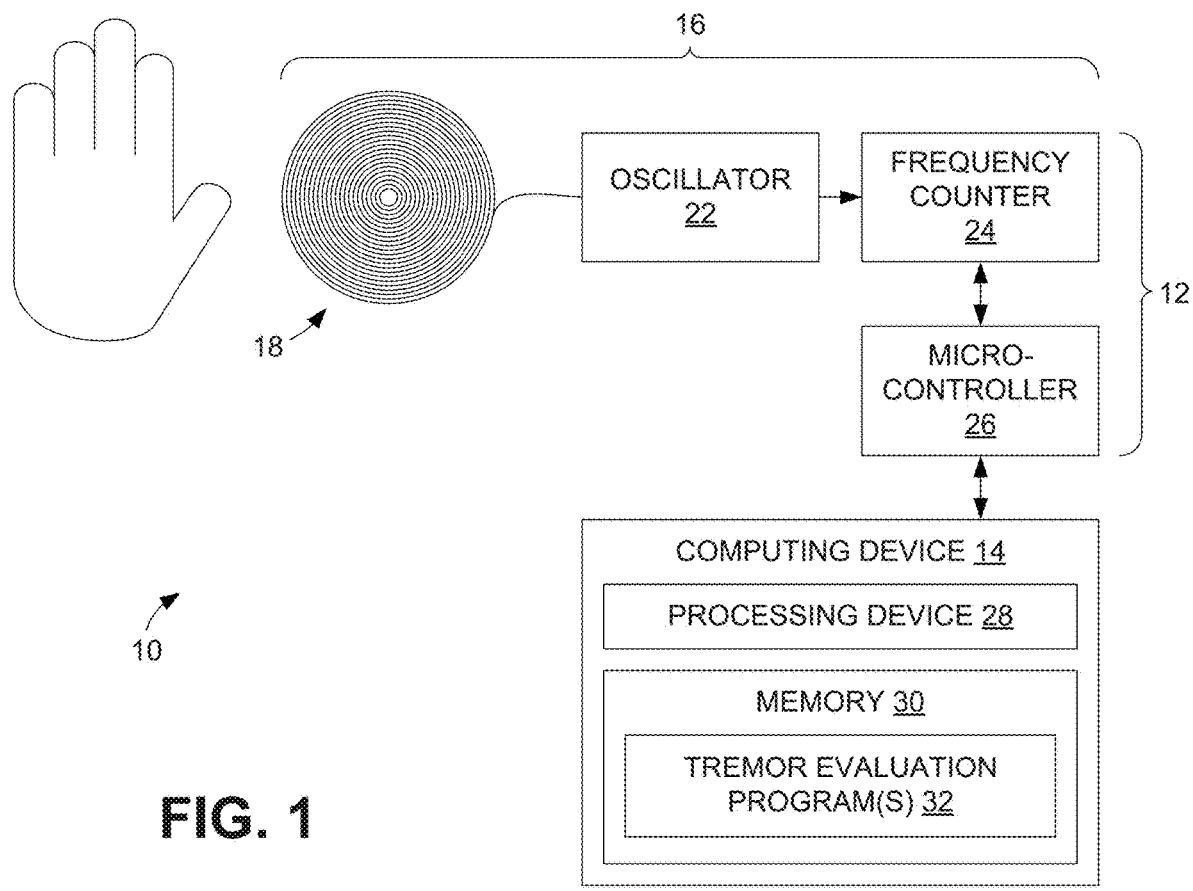
FIG. 1 is a schematic diagram of an embodiment of a system for detecting tremors.

FIG. 1 illustrates an embodiment of a tremor detection system 10. As shown in this figure, the system 10 generally comprises a contactless tremor detector 12 and a computing device 14 that is in electrical communication with the detector. In the embodiment of FIG. 1, the tremor detector 12 includes an oscillator circuit 16 having a sensing coil 18, an oscillator 22 connected to the coil, and a frequency counter 24 connected to the oscillator. The sensing coil 18 can comprise a spiral coil of conductive wire, such as copper wire. By way of example, the spiral coil can comprise approximately 50 turns of wire, an outer diameter of approximately 12 cm, and a measured inductance of approximately 110 μH.

In some embodiments, the oscillator 22 and the frequency counter 24 can be implemented as an integrated inductive sensor, such as an inductive sensing chip, which can be controlled by the microcontroller 26. In such cases, the inductive sensing chip can sense inductance and convert it into a digital signal that can be transmitted to the computing device 14 by the microcontroller 26. By way of example, the inductive sensing chip can comprise an LDC1000 and the microcontroller 26 can comprise an MSP430F5529, both of which are produced by Texas Instruments, Inc. In some embodiments, the oscillator circuit 16 can have a total capacitance of approximately 93 pF.

With further reference to FIG. 1, the computing device 14 comprises a processing device 28 and memory 30 (a nontransitory computer-readable medium) that stores a tremor evaluation program 32 (i.e., logic and/or computer-implementable instructions) that can receive the frequency counter data from the microcontroller 26 and generate information for an end user (e.g., physician) that can be used to diagnose a patient condition.

As shown in FIG. 1, a patient (or other user) can place his or her hand (or other body part to be evaluated) in proximity to the sensing coil 18 when an evaluation is to be performed. During operation of the system 10, the oscillator 22 generates oscillating electromagnetic fields that generate an eddy current density on the surface of a patient's hand when it is placed in proximity to the sensing coil 18. The magnetic fields generated by the eddy current are then coupled back to the sensing coil 18 and produce a difference current that changes the resonant frequency of the oscillator circuit 16. Generally speaking, the resonant frequency of the oscillator circuit 16 increases when the hand is brought closer to the sensing coil 18 and decreases when the hand is moved away from the coil. The resonant frequency changes are sensed by the frequency counter 24 and converted into digital frequency counter data that is provided to the microcontroller 26, which transmits them to the computing device 14.

Figure 5:
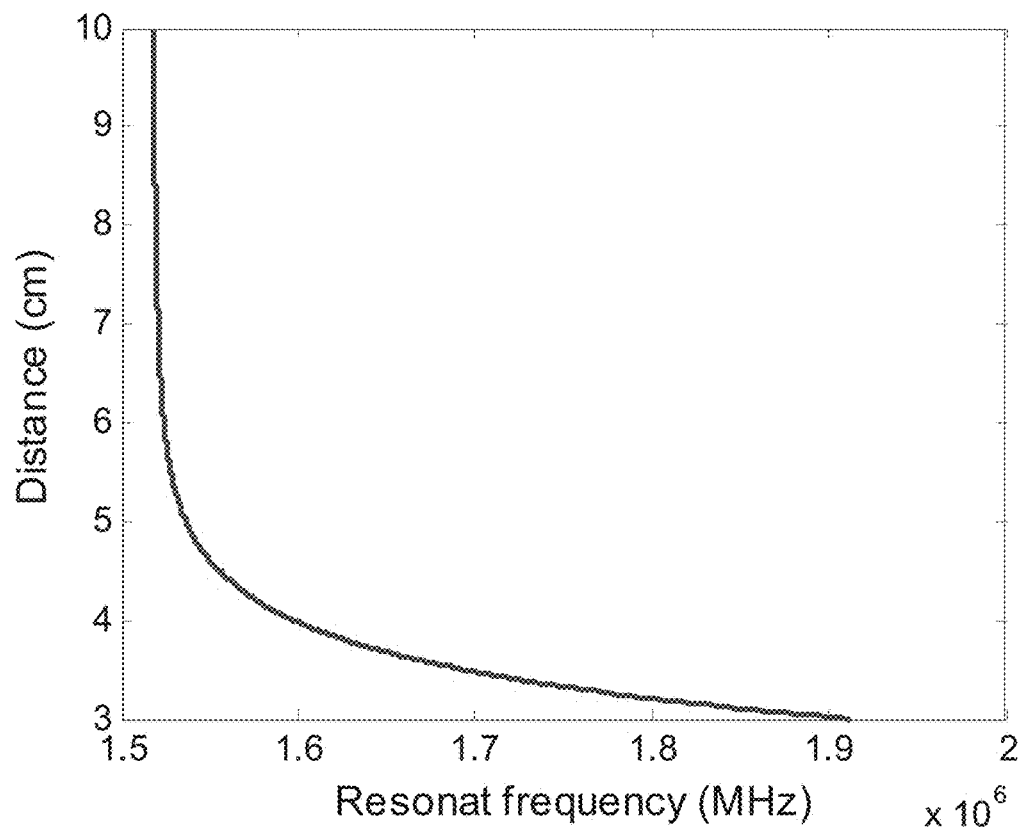
FIG. 5 is a graph that identifies distance as a function of the resonant frequency of an oscillation circuit of a tremor detectors.
Figure 7A:
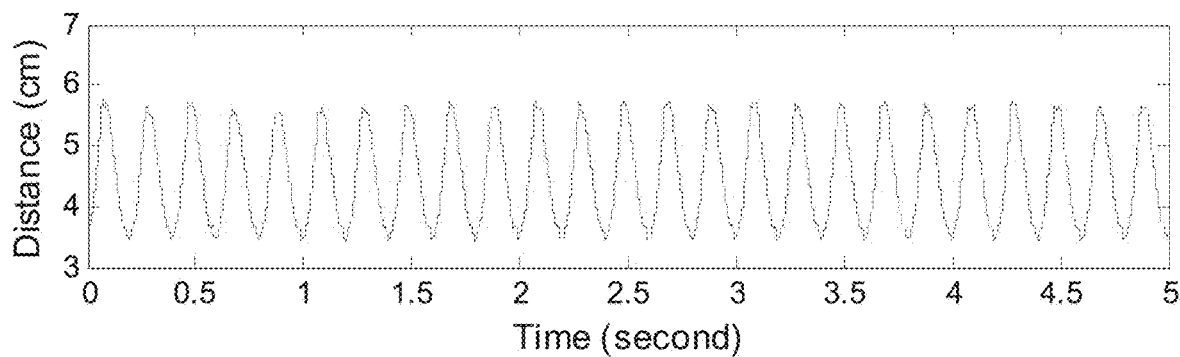
FIG. 7A is a graph that shows distance as a function of time when the wooden hand of FIG. 6 was actuated at 5 Hz.
Figure 7B:
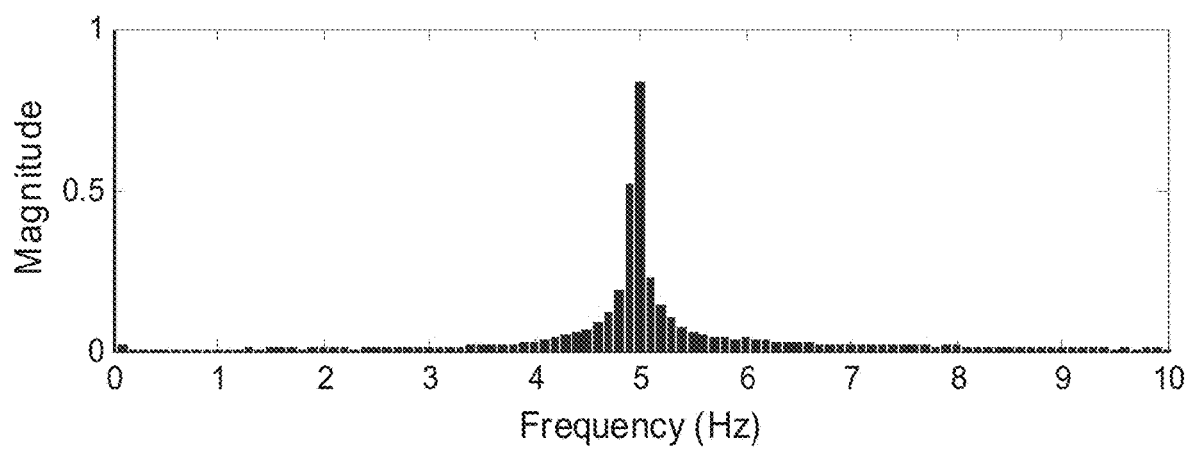
FIG. 7B is a graph that shows the spectral distribution of the distances of FIG. 7A.

In some embodiments, computing device 14 can correlate the frequency counter data into distances that vary with time. By way of example, the frequency counter data can be correlated to distances by an algorithm of the tremor evaluation program 32 using a correlation graph or table that is constructed during a calibration process in which the resonant frequency of the oscillation circuit 16 is measured as an object is placed distances from the sensing coil 18. FIG. 5 shows an example graph that correlates resonant frequency with distance. Through this process, the distance of the hand from the sensing coil 18 can be determined as a function of time (a temporal domain signal). This distance data in the temporal domain can then be converted into frequency data in the frequency domain that provide an indication of the frequency of any movement of the hand and, therefore, the frequency of any tremors that are being produced. In some embodiments, the distance data can be converted into frequency data by an algorithm of the tremor evaluation program 32 by performing a Fourier transform. FIG. 7B shows an example graph of hand movement frequencies obtained in this manner from distance data shown in FIG. 7A. The movement frequency data can then be evaluated by a physician for the purposes of diagnosing a condition of the patient. In particular, the physician can identify the frequency band that has the greatest amount of signal (power density). If this band falls within a frequency band associated with a particular condition, such as Parkinson's disease, the presence of the condition is indicated.

Figure 2:
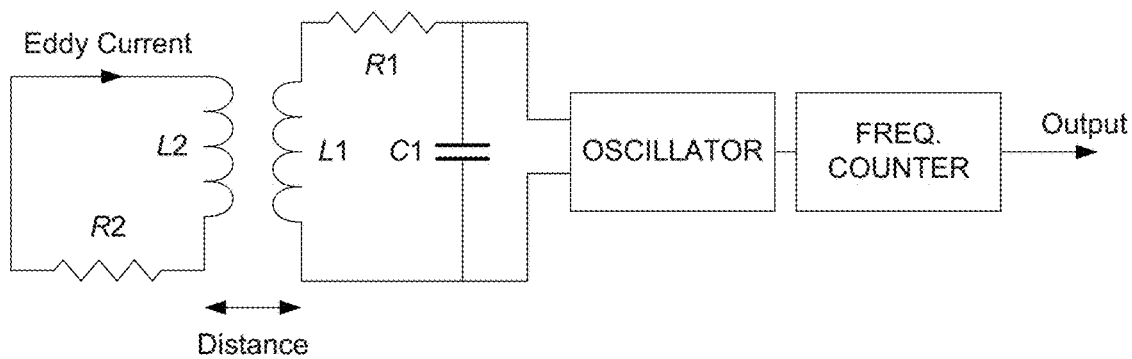
FIG. 2 is an equivalent circuit diagram of an oscillation circuit shown in FIG. 1.

FIG. 2 shows an equivalent circuit diagram for the oscillator circuit 16 shown in FIG. 1. In FIG. 2, L1 is the inductance of the sensing coil 18, C1 is the tuning capacitance of the coil, and R1 is the resistance of the coil. L2 is the inductance induced by the hand and R2 is the hand surface resistance. When the oscillator circuit 16 generates an alternating electromagnetic field, the eddy current density, J, is generated by the magnetic field on the hand. A magnetic field induced by the eddy current is then coupled back to the coil and produces a current, which changes the resonant frequency.

Figure 3:
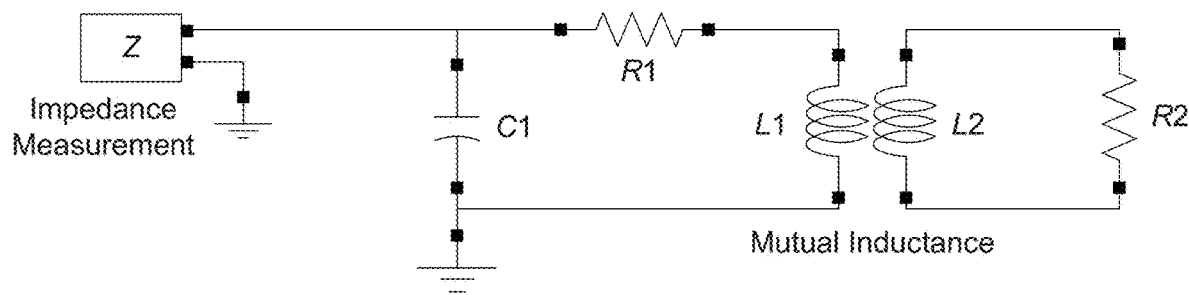
FIG. 3 is a schematic diagram of a simulation model of the oscillation circuit shown in FIG. 1.

FIG. 3 shows a simulation model for the oscillation circuit 16. The equivalent impendence can be expressed as $$Z = \frac{\frac{R_1}{\omega^2 C_1^2} + j\left(\frac{L}{\omega C_1^2} - \frac{R_1^2}{\omega C_1} - \frac{\omega L^2}{C_1}\right)}{R_1^2 + \left(\omega L - \frac{1}{\omega C_1}\right)} \text{ where} \quad (1)$$

$$L = L_1 - L_2 \frac{\omega^2 M^2}{R_2^2 + \omega^2 L_2^2},$$

ω is oscillator frequency, and M is the mutual inductance between the sensor coil and the human hand. In the simulation, C1=93 pF, L1=110 µH, and R1=0.165 Ω. According to the IEEE Standard 80, the internal resistance of the body is approximately as 300 Ω. An assumption was made that the internal resistance of human hand is R2=50 Ω and the inductance of the human hand is L2=20 µH. The working range between the hand and the detector was 3.5 to 10 cm.

Figure 4:
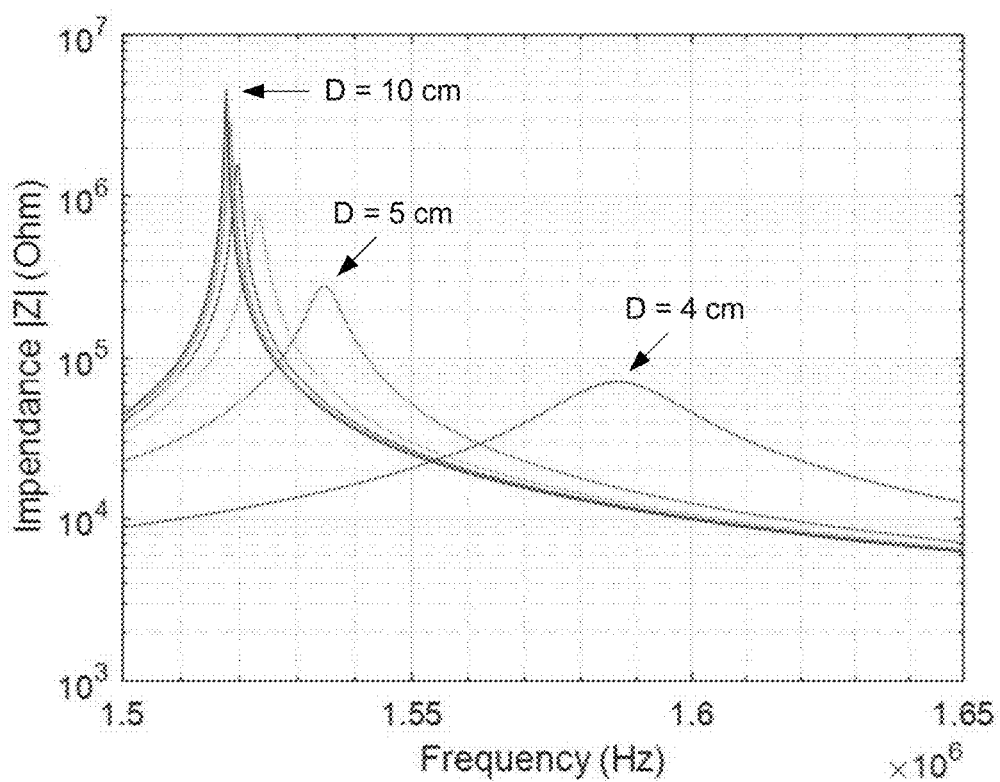
FIG. 4 is a graph that shows resonant frequencies at various distances, D, between a hand and a sensing coil of a tremor detector.

By the Bio-Savart law, the mutual inductance M is proportional to $1/D^3$ where D is the distance. When the mutual inductance increases, the resonant frequency in the inductive circuit increases. The impedance of the equivalent circuit is shown in FIG. 4.

The relationship between the distance and the resonant frequency is shown in FIG. 5. With the detected resonant frequency, the distance can be obtained. Through continuous counting of the resonant frequencies, the small variations between the coil and the hand can be dynamically obtained.

Figure 6:
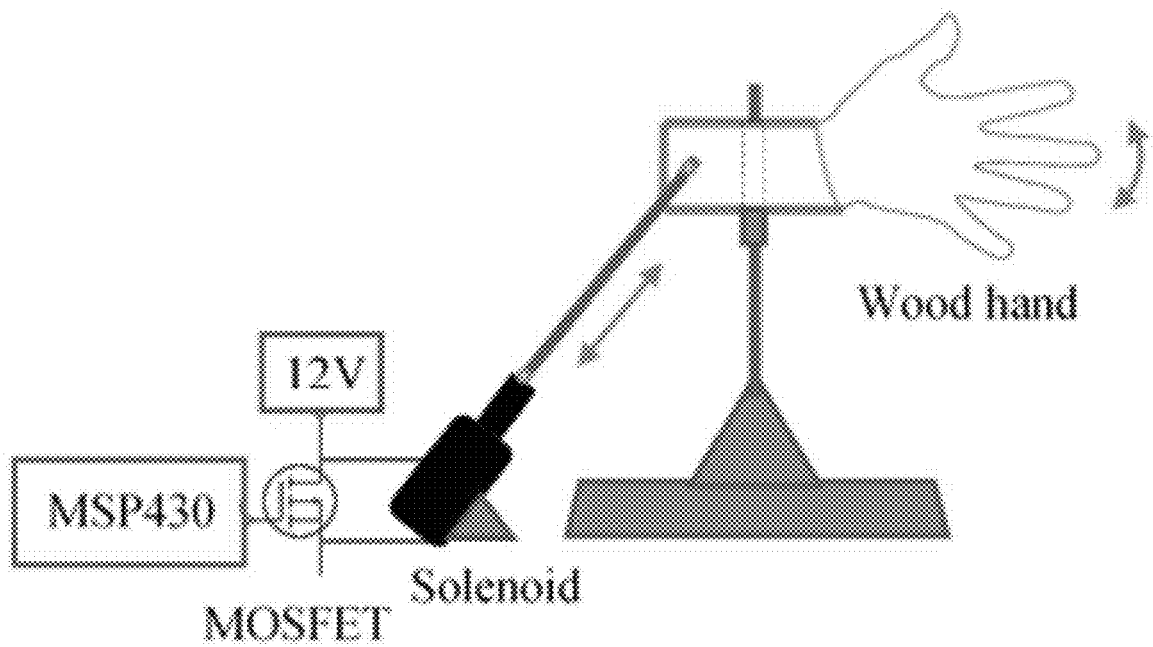
FIG. 6 is a schematic diagram of a testing apparatus used to manipulate a wooden hand.

Experimental apparatus was designed to verify the theory. As shown in FIG. 6, the apparatus consisted of a wooden hand wrapped in cooper foil to emulate a human hand as it is difficult to control the tremor frequency and magnitude of a real human hand. A solenoid actuator with a power requirement of 12 V and 1 A was used to actuate the wooden hand with a MOSFET (AO3414, 20 V, 4.2 A, N-Channel) to drive the actuator. An MSP430 microcontroller and a 12 V power supply were used for control. To mimic the movement of a real hand, the finger joints on the wooden hand model were loosened and were free to move when the hand is driven by the actuator. The swing magnitude of the wooden hand was approximately 2 cm. The wooden hand was placed in front of the sensing coil. Various actuation signals were tested.

When the wooden hand was placed 5 cm away from the sensing coil and the microcontroller produced 5 Hz signals to drive the wooden hand, continuous frequency counts at 10,000 samples/s and 24-bit resolution were acquired by the tremor detector. The frequencies were converted to a temporal plot in term of distance shown in FIG. 7A. The spectral distribution is shown in FIG. 7B. The motions from fingers contributed the spreading of the spectral distribution.

A triaxial accelerometer, which was configured on an eZ430-Chronos wireless wearable device (Texas Instruments, Inc.), was used to record the tremor accelerations of the wooden hand for purposes of comparison. The wearable device included a triaxial accelerometer (Bosch Sensortec BMA250), an RF transceiver (CC1101), and a microcontroller (MSP430F5509). The digital resolution of the triaxial accelerometer was 10 bits with a measurement range of ±16 g, a sensitivity of 16 LSB/g, and a zero-g offset of ±80 mg. The accelerometer sample rate was 33 samples/s for each axis.

Figure 8A:
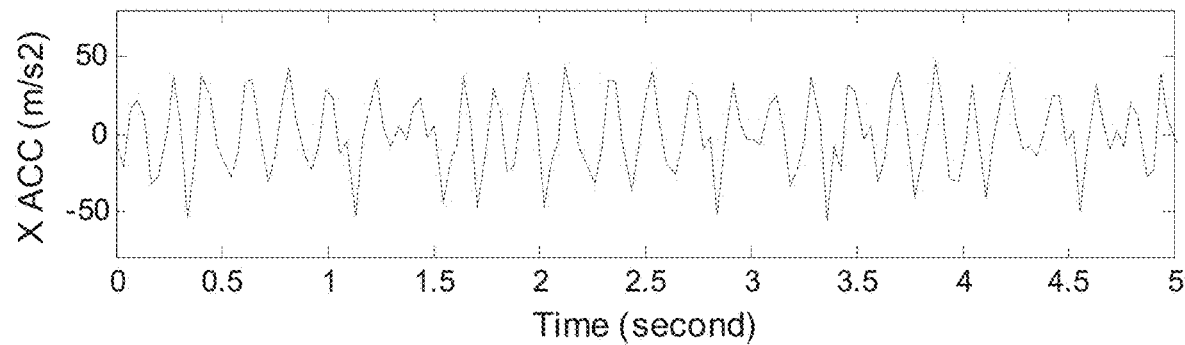
FIG. 8A is a graph that shows tremor acceleration at x axis as a function of time when the wooden hand was actuated at 5 Hz.
Figure 8B:
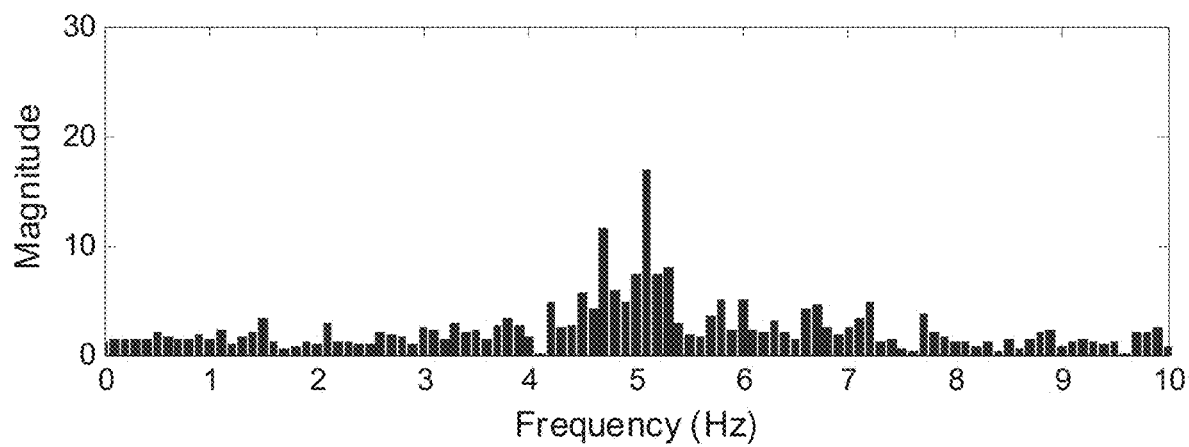
FIG. 8B is a graph that shows spectral distributions of the accelerations of FIG. 8A.
Figure 9A:
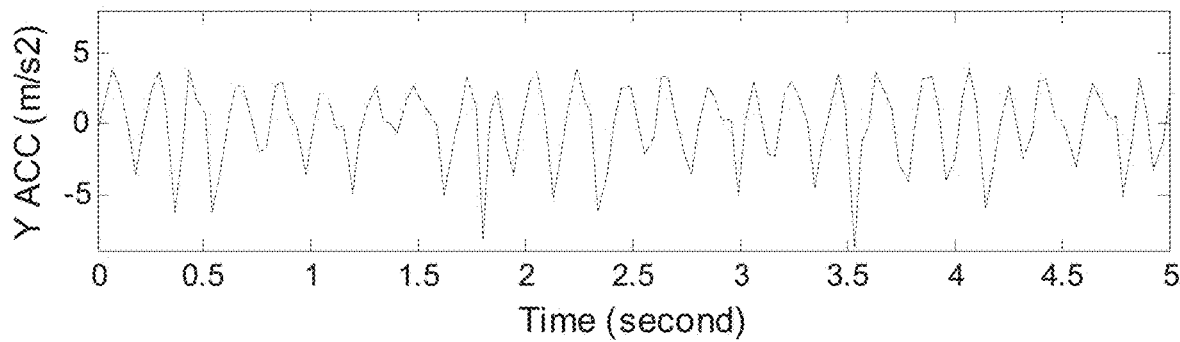
FIG. 9A is a graph that shows tremor acceleration at y axis as a function of time when the wooden hand was actuated at 5 Hz.
Figure 9B:
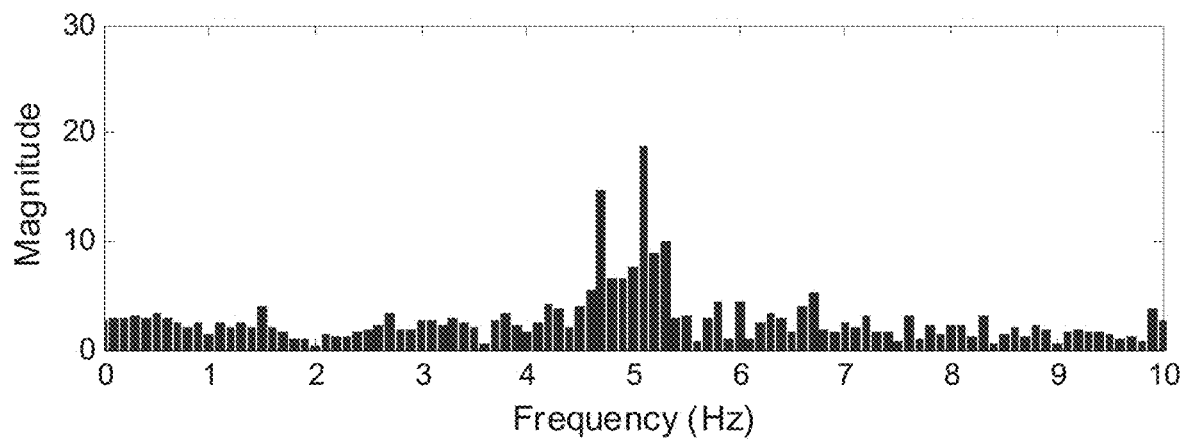
FIG. 9B is a graph that shows spectral distributions of the accelerations of FIG. 9A.
Figure 10A:
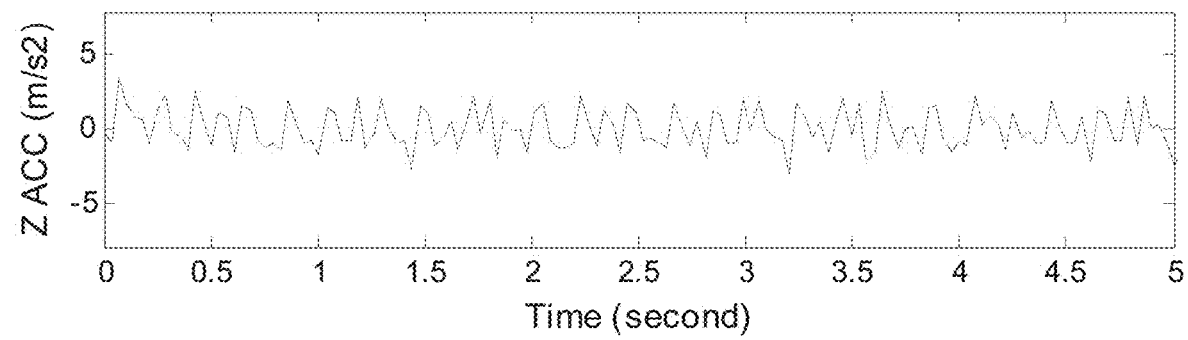
FIG. 10A is a graph that shows tremor acceleration at z axis as a function of time when the wooden hand was actuated at 5 Hz.
Figure 10B:
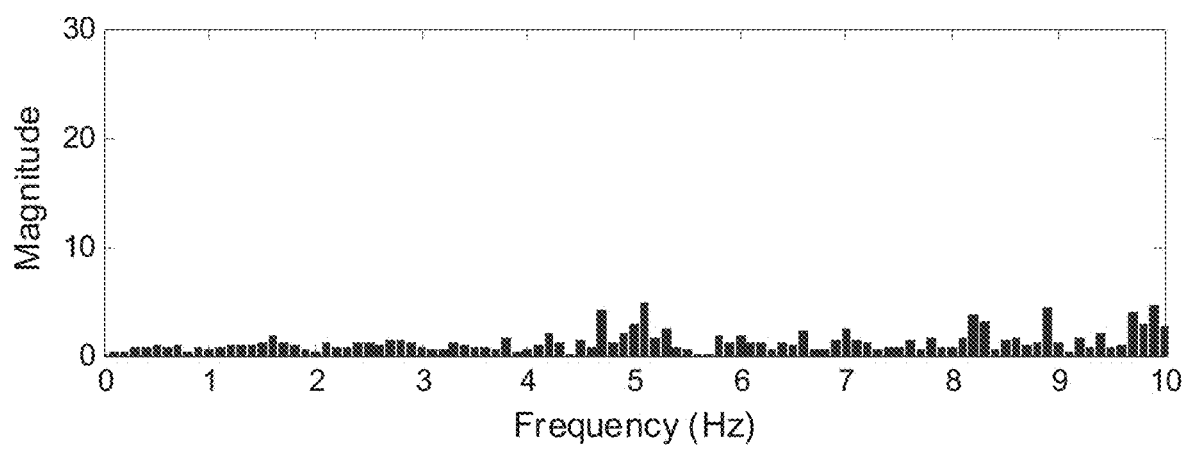
FIG. 10B is a graph that shows spectral distributions of the accelerations of FIG. 10A.

The device was attached on the palm of wooden hand. Accelerations of the hand were recorded when the hand was driven by the 5 Hz signal. Three sets of acceleration data are shown in FIGS. 8, 9, and 10. Comparing the spectral distributions in FIGS. 8B, 9B, and 10B with the one measured by the tremor detector, shown in FIG. 7B, only the signals from two axes can indicate the tremor signals. However, it is obvious that more harmonic elements were recorded. The temporal waveforms also showed distortion even though the hand model was moved with a single driving frequency. One reason for this is the low sample rate of the wearable device. However the main problem was that the accelerometers are designed to detect acceleration of an object, while the disclosed tremor detector detects the distance variations. This comparison demonstrates that the disclosed tremor sensor is better suited for detecting hand tremors when the subject consciously maintains his or her arm still such that the acceleration is not significant enough to be accurately detected.

The disclosed systems and methods can be used to quantify tremors associated with various diseases, such as fundamental tremors, Parkinson's disease, multiple sclerosis, stroke, traumatic brain injury, chronic kidney disease, and neurodegenerative diseases. In addition, tremors associated with other conditions or circumstances, such as anxiety, fear, fatigue from exercise, or the use or withdraw of drugs (such as amphetamines, cocaine, caffeine, corticosteroids, SSRI) and alcohol, can be detected. While the systems and methods have been described as being used to quantify hand tremors, it is noted that any body tremors can be measured using the systems and methods.

The invention claimed is:

1. A system for detecting tremors comprising:
a contactless tremor detector configured to be positioned in proximity to a body part of an individual without touching the body part, the tremor detector including an oscillator circuit having a sensing coil, an oscillator configured to generate alternating electromagnetic fields, and a frequency counter configured to sense a resonant frequency of the oscillator circuit as the resonant frequency changes in response to tremors of the body part of the individual adjacent to the sensing coil; and
a computing device configured to:
receive resonant frequency data from the contactless tremor detector,
convert the resonant frequency data into distance data, and
convert the distance data into frequency data that identifies a frequency at which the body part tremors.

2. The system of claim 1, wherein the oscillator and frequency counter are integrated together as an induction sensor.

3. The system of claim 2, wherein the induction sensor is configured to convert the resonant frequencies into digital resonant frequency data.

4. The system of claim 2, wherein the induction sensor comprises an induction sensing chip.

5. The system of claim 1, wherein the tremor detector further includes a microcontroller configured to receive resonant frequency data sensed by the frequency counter.

6. The system of claim 1, wherein the computing device is configured to convert the resonant frequency data into distance data using a correlation graph or table generated during a calibration process.

7. The system of claim 1, wherein the computing device is configured to convert the distance data into movement frequency data by performing a Fourier transform on the distance data.

8. A system for detecting tremors comprising:
a contactless tremor detector configured to be positioned in proximity to a body part of an individual without touching the body part, the tremor detector including a sensing coil, an oscillator in electrical communication with the sensing coil configured to deliver a signal to the sensing coil that causes the sensing coil to generate alternating electromagnetic fields that create an eddy current on a surface of the body part placed in proximity to the sensing coil, wherein magnetic fields generated by the eddy current couple back to the sensing coil and change a resonant frequency of the oscillator, a frequency counter configured to sense the resonant frequency of the oscillator as the resonant frequency changes in response to tremors of the body part, and a microcontroller configured to receive resonant frequency data from the oscillator circuit, and
a computing device configured to receive the resonant frequency data from the microcontroller, convert the resonant frequency data into distance data that indicates a distance of the body part from the sensing coil as a function of time, and convert the distance data into movement frequency data that identifies a frequency at which the body part tremors.

9. The system of claim 8, wherein the computing device is configured to convert the resonant frequency data into distance data using a correlation graph or table generated during a calibration process.

10. The system of claim 8, wherein the computing device is configured to convert the distance data into movement frequency data by performing a Fourier transform on the distance data.

* * * * *